US009574178B2

(12) United States Patent
Mitchell et al.

(10) Patent No.: US 9,574,178 B2
(45) Date of Patent: Feb. 21, 2017

(54) MEGAKARYOCYTE AND PLATELET PRODUCTION FROM STEM CELLS

(75) Inventors: W. Beau Mitchell, New York, NY (US); Mauro P. Avanzi, New York, NY (US)

(73) Assignee: New York Blood Center, Inc., New York, NY (US)

(*) Notice: Subject to any disclaimer, the term of this patent is extended or adjusted under 35 U.S.C. 154(b) by 0 days.

(21) Appl. No.: 13/422,413

(22) Filed: Mar. 16, 2012

(65) Prior Publication Data
US 2012/0238020 A1 Sep. 20, 2012

Related U.S. Application Data

(60) Provisional application No. 61/454,415, filed on Mar. 18, 2011.

(51) Int. Cl.
*C12N 5/078* (2010.01)
*C12M 1/00* (2006.01)

(52) U.S. Cl.
CPC ............ *C12N 5/0644* (2013.01); *C12M 23/58* (2013.01); *C12M 47/02* (2013.01); *C12N 2500/02* (2013.01); *C12N 2501/125* (2013.01); *C12N 2501/145* (2013.01); *C12N 2501/21* (2013.01); *C12N 2521/00* (2013.01)

(58) Field of Classification Search
None
See application file for complete search history.

(56) References Cited

U.S. PATENT DOCUMENTS

| 2010/0248361 A1 | 9/2010 | Lasky et al. |
| 2012/0014933 A1 | 1/2012 | Baruch et al. |
| 2012/0028275 A1 | 2/2012 | Kieferle et al. |
| 2012/0028352 A1 | 2/2012 | Oh et al. |

FOREIGN PATENT DOCUMENTS

EP 2298865 A1 3/2011

OTHER PUBLICATIONS

Mostafa et al. "Oxygen tension influences the differentiation, maturation and apoptosis of human megakaryocytes", British Journal of Haematology 111: 879-889, 2000.*
Dunois-Larde et al. "Exposure of human megakaryocytes to high shear rates accelerates platelet production", Blood 114(9): 1875-1883, 2009.*
Choi et al. "Hematopoietic and endothelial differentiation of human induced pluripotent stem cells", Stem Cells 27: 559-567, 2009.*
Boitano et al. "Aryl hydrocarbon receptor antagonists promote the expansion of human hematopoietic stem cells", Science 329: 1345-8, Sep. 2010.*
Watts et al. "Combination of HOXB4 and Delta-1 ligand improves the expansion of cord blood cells" Blood 116(26): 5859-5866, Dec. 2010.*
Clarke et al. "Compartmentalized megakaryocyte death generates functional platelets committed to caspase-independent death", Journal of Cell Biology 160(4): 577-587, 2003.*
Chang et al. "Proplatelet formation is regulated by the Rho/ROCK pathway" Blood 109(10): 4229-36, 2007.*
Battinelli et al. "Delivering new insight into the biology of megakaryopoisis and thrombopoiesis", Current Opinion in Hematology 14: 419-426, 2007.*
Feugier et al. "Ex vivo expansion of stem and progenitor cells in co-culture of mobilized peripheral blood CD34+ cells on human endothelium transfected with adenovectors expressing thrombopoietin, c-kit ligand, and Flt-3 ligand", Journal of Hematotherapy & Stem Cell Research 11: 127-38, 2002.*
Matsunaga et al. "Ex vivo large-scale generation human platelets from cord blood CD34+ cells", Stem Cells 2877-2887, 2006.*
Dolzhanskiy et al. "The development of human megakaryocytes: III. Development of mature megakaryocytes from highly purified committed progenitors in synthetic culture media and inhibition of thrombopoietin-induced polyploidization by interleukin-3", Blood 89(2): 426-434, 1997.*
Feng Yi, et al. "An effective and simple expansion system for megakaryocyte progenitor cells using a combination of heparin with thrombopoietin and interleukin-11", Experimental Hematology 33(12): 1537-1543, 2005.*
Aguila JR, et al. "SALL4 is a robust stimulator for the expansion of hematopoietic stem cells," Blood 118:576-585, 2011.
Avecilla ST et al. "Chemokine-mediated interaction of hematopoietic progenitors with the bone marrow vascular niche is required for thromopoiesis." Nature Med. 10:64-71, 2004.
Balduini A et al. "Adhesive receptors, extracelllular proteins and myosin IIA orchestrate proplatelet formation by human megakaryocytes." J. Throm. Haemost. 6:1900-1907, 2008.
Clarke MCH et al. "Compartmentalized megakarocyte death generates function platelets committed to caspase-independent death." J. Cell Bio. 160:577-587, 2003.
Conant CG et al. "Platelet adhesion and aggregation under flow using microfluidic flow cells." J. Visualized Exp. 32, 2009, http://www.jove.com/details.php?id=1644.
Gandhi MJ et al. "A novel strategy for generating platelet-like fragments from megakaryocytic cell lines and human progenitor cells." Blood Cells Mol. Dis. 35:70-73, 2005.
Giammona LM et al. "Nicotinamide (vitamin B3) increases the polyploidisation and proplatelet formation of cultured primary human megakaryocytes." Br. J. Haematol. 135:554-66, 2006.
Junt T et al. "Dynamic visualization of thrombopoiesis within bone marrow." Science 317:1767-1770, 2007.
Kaplan RN et al. "Niche-to-niche migration of bone-marrow-derived cells." Trends Mol. Med. 13:72-81, 2007.
Kopp HG and Rafii S "Thrombopoietic cells and the bone marrow vascular niche." Ann. N. Y. Acad. Sci. 1106:175-9, 2007.
Legendre P et al. "CHO cells expressing the high affinity alpha (IIb)beta3 T562N integrin demonstrate enhanced adhesion under shear." J. Thromb. Haemost. 4:236-46, 2006.

(Continued)

*Primary Examiner* — Emily Cordas
(74) *Attorney, Agent, or Firm* — K&L Gates LLP; Louis C. Cullman; Michelle Glasky Bergman

(57) ABSTRACT

Methods for obtaining purified populations of megakaryocytes and platelets by ex vivo culture of stem cells are provided herein.

11 Claims, 5 Drawing Sheets

(56) References Cited

OTHER PUBLICATIONS

Liu Y et al. "Ex vivo expansion of hematopoietic stem cells derived from umbilical cord blood in rotating wall vessel." J. Biotechnol. 124:592-601, 2006.

Lordier L et al. "Megakaryocyte endomitosis is a failure of late cytokinesis related to defects in the contractile ring and Rho/Rock signaling." Blood 112:3164-3174, 2008.

Mekrache M et al. "Activation of recombinant alphaIIbbeta3 expressed in Chinese hamster ovary cells exposes different binding sites for fibrinogen or von Willebrand factor: evidence using monoclonal antibodies to alphaIIbbeta3." Br. J. Haematol. 116:636-644, 2002.

Norol F et al. "Effects of cytokines on platelet production from blood and bone marrow CD34+ cells." Blood 91:830-843, 1998.

Panuganti S et al. "Bone marrow niche-inspired, multiphase expansion of megakaryocytic progenitors with high polyploidization potential," Cytotherapy 12:767-782, 2010.

Sangeetha VM et al. "Expansion of cord blood CD34+ cells in presence of zVADfmk and zLLYfmk improved their in vitro functionality and in vivo engraftment in NOD/SCID mouse." PLoS One 5:e12221, 2010.

Siddiqui NF et al. "Enhanced generation of megakaryocytes from umbilical cord blood-derived CD34(+) cells expanded in the presence of two neutraceuticals, docosahexanoic acid and arachidonic acid, as supplements to the cytokine-containing medium." Cytotherapy 13:114-28, 2011.

Slayton WB et al. "Developmental differences in megakaryocyte maturation are determined by the microenvironment." Stem Cells 23:1400-8, 2005.

Sullenbarger B. et al. "Prolonged continuous in vitro human platelet production using 3D scaffolds." Exp. Hematol. 37:101-110, 2009.

Sun S et al. "Overexpression of cyclin D1 moderately increases ploidy in megakaryocytes." Haematologica 86:17-23, 2001.

Szabo E et al. "Direct conversion of human fibroblasts to multilineage blood progenitors." Nature 468:521-6, 2010.

Valeri CR et al. Freezing human platelets with 6 percent dimethyl sulfoxide with removal of the supernatent solution before freezing and storage at −80 degrees C without postthaw processing. Transfusion 45:1890-8, 2005.

Yang M et al. "Promoting effects of serotonin on hematopoiesis: ex vivo expansion of cord blood CD34+ stem/progenitor cells, proliferation of bone marrow stromal cells, and antiapoptosis." Stem Cells 25:1800-1806, 2007.

Zimmet JM et al. "A role for cyclin D3 in the endomitotic cell cycle." Mol. Cell. Bio. 17:7248-7259, 1997.

Battinelli E et al. "Nitric oxide induces apoptosis in megakaryocyte cell lines." Blood 95:3451-59, 2000.

Chen Z et al. "The May-Hegglin anomaly gene MYH9 is a negative regulator of platelet biogenesis modulated by the Rho-ROCK pathway." Blood 110:171-179, 2007.

Lee DH et al. "Platelet substitutes and novel platelet products." Exp. Opin. Invest. Drugs 9:457-469, 2000.

Pallotta I et al. "Bone marrow osteoblastic niche: a new model to study physiological regulation of megakaryopoiesis." PLoS One 4:e8359, 2009.

Reems JA et al. "In vitro megakaryocyte production and platelet biogenesis: state of the art." Trasfus. Med. Rev. 24:33-43, 2010.

Schulze H et al. "Characterization of the megakaryocyte demarcation membrane system and its role in thrombopoiesis." Blood 107:3868-3875, 2006.

Topp et al., Culture of isolated bovine megakaryocytes on reconstituted basement membrane matrix leads to proplatelet process formation, Blood 76:912-924, 1990.

Choi et al., "Platelets generated in vitro from proplatelet-displaying human megakaryocytes are functional," Blood 85:402-413, 1995.

Cheng et al., Human mesenchymal stem cells support megakaryocyte and pro-platelet formation from CD34+ hematopoietic progenitor cells. Journal of Cellular Physiology, 184: 58-69 (2000).

Lasky et al., Manipulation of oxygenation and flow-induced shear stress can increase the in vitro yield of platelets from cord blood. Tissue Engineering Part C: Methods, vol. 17, No. 11, pp. 1081-1088 (2011).

Pallotta et al., Three-dimensional system for the in vitro study of megakaryocytes and functional platelet production using silk-based vascular tubes. Tissue Engineering Part C: Methods, vol. 17, No. 12, pp. 1223-1232 (2011).

Thon et al., Cytoskeletal mechanics of proplatelet maturation and platelet release. Journal of Cell Biology, vol. 181, No. 4, pp. 861-874 (2010).

Extended European Search Report for European Patent Application Serial No. 12761310, Aug. 29, 2014.

* cited by examiner

MEGAKARYOCYTE AND PLATELET PRODUCTION FROM STEM CELLS

CROSS REFERENCE TO RELATED APPLICATIONS

This application claims the benefit under 35 U.S.C. §119 (e) of United States Provisional Patent Application 61/454,415 filed Mar. 18, 2011, the entire contents of which are incorporated by reference herein.

FIELD OF THE DISCLOSURE

The present disclosure is drawn to in vitro methods of producing platelets from stem cells for clinical use.

BACKGROUND OF THE DISCLOSURE

Each year, millions of patients in the United States are affected by various blood disorders and diseases, such as thrombocytopenia (low platelet number), that require multiple treatments of platelet transfusions. Although more than 10 million platelet donations are made annually (all of which come from volunteer donors) the demand continues to increase at a greater rate than the supply. The process of obtaining platelets, however, is not only lengthy and costly, but it is further limited by a shelf life of only a few days. This short window of usability means that many donated platelet units are discarded before having an opportunity to serve the patients in need of these valuable products.

Platelets are tiny blood cells that perform the vital and highly specialized function of blood clotting. Almost a trillion platelets circulate in the average person's blood, and the turnover is such that the entire platelet population is replaced every 10 days. This represents a tremendous amount of ongoing platelet production. Platelets have a highly organized cytoskeleton and intracellular stores of over 300 proteins, which they secrete at sites of blood vessel injury. Platelets also play a role in inflammation, blood vessel growth, and tumor metastasis.

Platelets (thrombocytes) are small, irregularly shaped clear cell fragments 2-3 μm in diameter, which are derived from fragmentation of precursor megakaryocytes. Megakaryocytes are derived from hematopoietic stem cell precursor cells in the bone marrow These multipotent stem cells live in the marrow sinusoids and are capable of producing all types of blood cells depending on the signals they receive. The primary signal for megakaryocyte production is thrombopoietin (TPO). TPO induces differentiation of progenitor cells in the bone marrow towards a final megakaryocyte phenotype. The megakaryocyte develops through the following lineage: CFU-ME (pluripotential hemopoietic stem cell or hemocytoblast)→megakaryoblast→promegakaryocyte→megakaryocyte. The cell eventually reaches megakaryoblast stage and loses its ability to divide. However, it is still able to replicate its DNA and continue development, becoming polyploid. The cytoplasm continues to expand and the DNA complement can increase to greater than 64 N.

Once the cell has completed differentiation and becomes a mature megakaryocyte, it begins the process of producing platelets. TPO plays a role in inducing the megakaryocyte to form small proto-platelet processes. Platelets are held within these internal membranes within the cytoplasm of the megakaryocytes. There are two proposed mechanisms for platelet release. In one scenario, these proto-platelet processes break up explosively to become platelets. Alternatively, the cell may form platelet ribbons into blood vessels. The ribbons are formed via pseudopodia and they are able to continuously emit platelets into circulation. In either scenario, each of these proto-platelet processes can give rise to 2000-5000 new platelets upon breakup. Overall, more than 75% of these newly-produced platelets will remain in circulation while the remainder will be sequestered by the spleen.

Thrombocytopenia, a major medical problem affecting millions of patients per year in the US, can result in spontaneous bleeding and is treated using various methods to increase platelet production. The condition can result from malignancy and chemotherapy, immune disorders such as immune thrombocytopenia (ITP), infection, and major surgery. There are also a large number of inherited platelet defects that cause excessive bleeding. All of these serious medical conditions may require treatment at some point with life-saving platelet transfusions There has been much interest in the possibility of using stem cells to produce platelets in the laboratory for clinical use. Stem cells are undifferentiated cells in early stage of development and capable of giving rise to more cells of the same type or differentiating into a diverse range of cell lineages. The main different types of stem cells are human embryonic stem cells (HeSC), induced pluripotent stem cells (IPSO) and hematopoietic stem cells (HSC).

HeSC are pluripotent stem cells derived from the inner cell mass of an early-stage embryo and are capable of differentiating into all derivatives of the three primary germ layers: ectoderm, endoderm and mesoderm. These cells are capable of differentiating into all kinds of cells in the human body. IPSO are a type of pluripotent stem cell artificially derived from a mature cell. Typically, adult somatic cells are induced to become pluripotent by activating specific genes of immaturity in these cells. Hematopoietic stem cells are progenitor cells that circulate in the blood and reside in the bone marrow and have the potential to give rise to all hematopoietic cells. Hematopoietic stem cells can be acquired from the bone marrow, peripheral blood with apheresis machines, or from umbilical cord or placenta after birth.

Culture systems have been described for differentiating stem cells into the various types of blood cells. There were expectations that stem cells, such as hematopoietic, HeSC and IPSO, could be used to generate blood cells for clinical use. However, using the currently available methods, the yield is far too low for clinical use. As an example, one unit of umbilical cord blood may contain about $10^6$ (one million) CD34+ cells. One million CD34+ cells yield up to $10^7$ platelets under current optimal conditions. In contrast, a typical platelet transfusion delivers about $3 \times 10^{11}$ platelets. Thus, a 10,000 fold increase in efficiency is needed to provide a transfusion of cultured platelets to equal the number of platelets from one unit of umbilical cord blood.

SUMMARY OF THE DISCLOSURE

Disclosed herein are methods and systems for the ex vivo production of megakaryocytes and platelets from stem cells.

In one embodiment disclosed herein, a method is provided for producing platelets in vitro comprising (1) selecting and culture-expanding megakaryocyte progenitor and/or stem cells, (2) differentiating the expanded cells into megakaryocytes, (3) maturing the megakaryocytes in an artificial bone marrow niche environment, (4) stimulating proplatelet formation and platelet release from the mature megakaryocytes, and (5) collecting the platelets. In another embodiment, the megakaryocyte progenitor and/or stem cells are selected from the group consisting of hematopoietic stem cells (from umbilical cord blood, peripheral and bone marrow), induced pluripotent stem cells (IPSO), human embryonic stem cells (HeSC), and human fibroblasts. Stem cells selected from these different sources are differentiated into megakaryocytes and stimulated to release platelets. In another embodiment, the stem cells are enriched for CD34+ cells prior to culture-expansion.

Optionally, mature megakaryocytes are isolated from the maturing culture and the mature megakaryocytes are used for platelet production and immature megakaryocytes are returning to the maturation culture.

In yet another embodiment, the stem cell expansion culture is conducted in the presence of a first growth medium comprising plurality of growth factors selected from the group consisting of aryl-hydrocarbon inhibitor/stem regenin-1, notch-ligand delta-1, prostaglandin-E2, Sal-like protein 4 (SALL4) gene activators, p38 inhibitors (such as SB203580), homeobox protein Hoxb4 activators, stromal cell-derived factor-1 (SDF-1α), histone acetyltransferase inhibitors (HAI, such as garcinol), valproic acid, co-culture with mesenchymal stem cells, endothelial and/or OP-9 (bone marrow-derived mouse stromal cells) cells, tropoelastin, copper chelation, benzyloxycarbonyl-Val-Ala-Asp (OMe) fluoromethylketone (Z-VAD-FMK), banana lectin, garlic lectin, interferon-α, thrombopoietin (TPO), stem cell factor (SCF), interleukin (IL)-3, IL-6, IL-11, FLT-3 ligand (FLT-3l), IGF-1, erythropoietin (EPO), dexamethasone, and lipids. In yet another embodiment, the growth factors are TPO, SCF, IL-3, IL-6, and IL-11.

In another embodiment, megakaryocyte expansion is conducted in a second medium comprising a plurality of growth factors selected from the group consisting of serotonin, arachidonic acid, Z-VAD-FMK, TPO, SCF, IL-3, IL-6, and FLT-3l.

Megakaryocyte maturation (polyploidization) is conducted in a cell growth matrix and a third medium comprising a plurality of growth factors selected from the group consisting of nicotinamide, folic acid, vitamin B12, Rho/Rock inhibitors, Src inhibitors, Aurora-B inhibitors, Bcr-Abl inhibitors, phorbol 12-myristate 13-acetate (PMA), blebbistatin, a stathmin inhibitor (staurosporine), myosin light chain kinase (MLCK) inhibitors and under conditions of increased oxygen concentration, between about 10% and about 30% $PO_2$. In another embodiment second the cell growth matrix is collagen I. In yet another embodiment, the growth factors are nicotinamide and a Rho/Rock inhibitor. In still another embodiment, the Rho/Rock inhibitor is Y27632.

In another embodiment, the proplatelet formation and platelet release steps are conducted in an artificial three-dimensional (3D) bone marrow niche environment. The 3D bone marrow niche environment is comprised of alginate or polystyrene beads, mesh, felt or other 3D structure, coated with a plurality of growth factors selected from the group consisting of fibrinogen, fibronectin, von Willebrand factor (vWF), Fas-ligand, PMA, nitric oxide, Rho/Rock inhibitors, Src inhibitors, Rac1 inhibitors, CDC42 inhibitors, SDF-1α, hirudin, heparin, c-Myc inhibitors, MLCK inhibitors, and Rho/Rock inhibitors. Shear stress is applied with a flow system (syringe pumps) to the 3-D matrix to improve platelet release. Tangential flow systems and membranes with 3-5 μm pores are also suitable.

Also disclosed herein is a method for producing platelets in vitro comprising (1) culturing stem cells in a first growth medium to produce a megakaryocyte progenitor cell population; (2) maturing the expanded megakaryocyte progenitor cells in an artificial bone marrow niche environment comprising a second growth medium in the presence of an oxygen concentration between about 10% and about 30% $PO_2$ to differentiate the megakaryocyte progenitor cells into megakaryocytes; (3) isolating the mature megakaryocytes; (4) culturing the mature megakaryocytes in a three-dimensional matrix and a third growth medium and in the presence of an oxygen concentration between about 10% and about 30% $PO_2$ and a shear stress between about 100 and 400 μl/min to produce platelets; and (5) collecting the platelets.

In another embodiment, the stem cells are selected from the group consisting of hematopoietic stem cells, induced pluripotent stem cells, embryonic stem cells, and fibroblasts. In yet another embodiment, the hematopoietic stem cells are obtained from the bone marrow, peripheral blood, or cord blood. In another embodiment, the stem cells are enriched for CD34+ cells prior to culture-expansion.

In another embodiment, the first growth medium comprises a plurality of growth factors selected from the group consisting of aryl-hydrocarbon inhibitor/stem regenin-1, notch-ligand delta-1, prostaglandin-E2, SALL4 gene activators, Hoxb4 activators, stromal cell-derived factor-1 (SDF-1α), histone acetyl transferase inhibitors, valproic acid, co-culture with mesenchymal stem cells and/or OP-9 cells, tropoelastin, copper chelation, Z-VAD-FMK, banana lectin, garlic lectin, interferon-α, thrombopoietin (TPO), p38 inhibitors, stem cell factor (SCF), dexamethasone, lipids, IGF-1, erythropoietin (EPO), IL-3, IL-6, IL-11, and FLT-3 ligand (FLT-3l). In another embodiment, the growth factors are TPO, SCF, IL-3, IL-6, and IL-11.

In another embodiment, the second growth medium comprises a plurality of growth factors selected from the group consisting of serotonin, arachidonic acid, Z-VAD-FMK, TPO, SCF, IL-3, IL-6, FLT-3l, nicotinamide, and a Rho/Rock inhibitor. In an other embodiment, the growth factors are nicotinamide and a Rho/Rock inhibitor.

In another embodiment the cell growth matrix is selected from the group consisting of extracellular matrix extracts, extracellular matrix gels, gelatin, fibrinogen, collagen, methylcellulose, and combinations thereof.

In another embodiment, the artificial bone marrow niche further contains mesenchymal stem cells and/or endothelial cells.

In another embodiment, the third growth medium comprises a plurality of growth factors selected from the group consisting of fibrinogen, fibronectin, von Willebrand factor (vWF), Fas-ligand, PMA, nitric oxide, MLCK inhibitors, Rho/Rock inhibitors, Src inhibitors, SDF-1α, nicotinamide, folic acid, vitamin B12, Rho/Rock inhibitors, Src inhibitors, Aurora-B inhibitors, Bcr-Abl inhibitors, phorbol 12-myristate 13-acetate (PMA), blebbistatin, and MLCK inhibitors. In yet another embodiment, the growth factors are fibrinogen, fibronectin, vWF, Fas-ligand, a MLCK inhibitor and a Rho/Rock inhibitor.

Also disclosed herein is a platelet production system for the ex vivo production of platelets comprising: a bioreactor for expansion of stem cells in the presence of a first growth medium in fluid communication with; a maturation chamber comprising an artificial bone marrow niche and a second growth medium, wherein the maturation chamber is in fluid communication with; a cell separation chamber for selecting mature megakaryocytes which is in fluid communication with; a platelet production module comprising a plurality of platelet production chambers, a three-dimensional matrix, a third growth medium, and a plurality of pumps for moving the third growth medium across the platelet production chambers, wherein the platelet production module is in fluid communication with; a platelet collection chamber.

DETAILED DESCRIPTION OF THE DISCLOSURE

Figure 1:
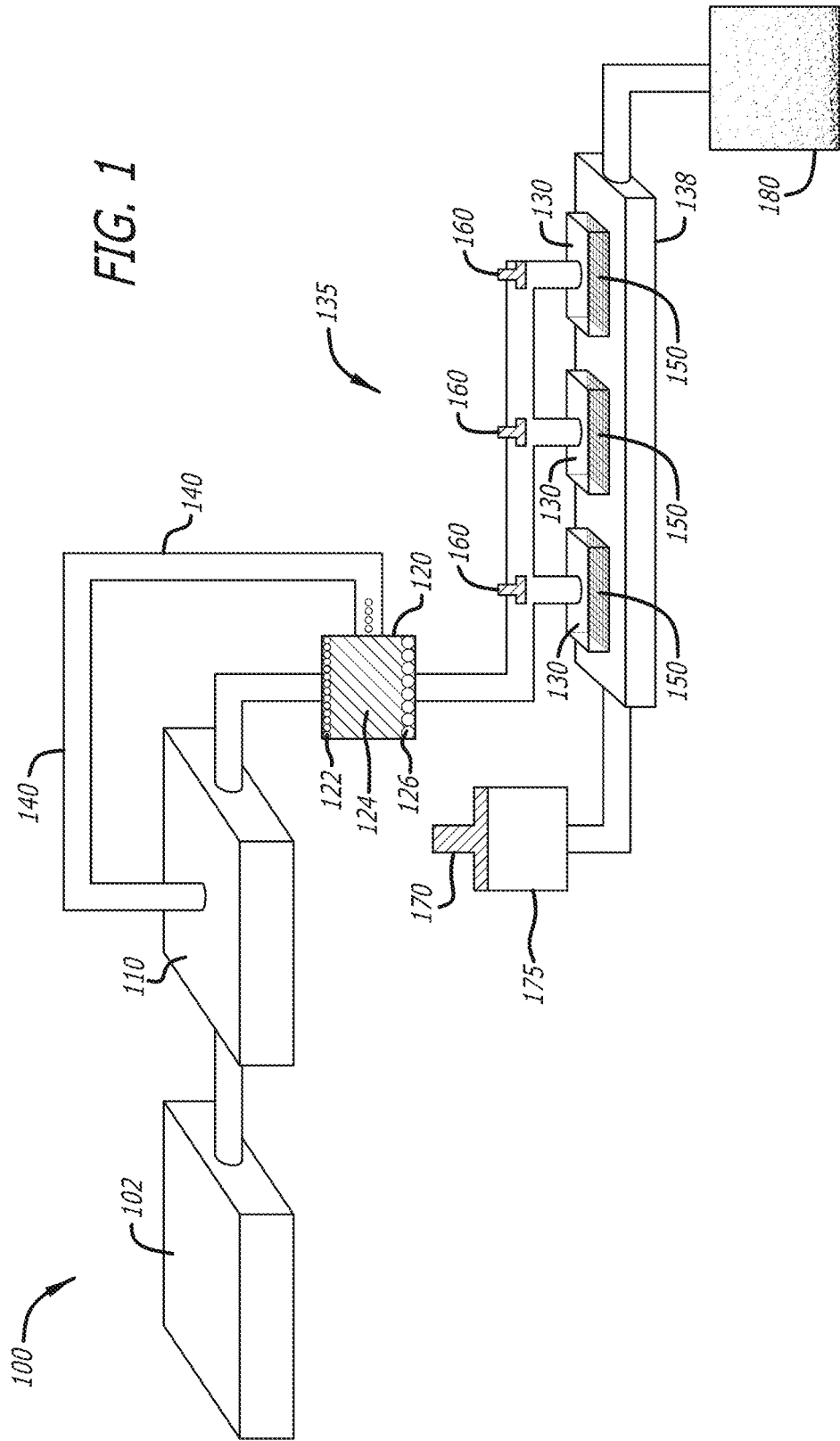
FIG. 1 depicts a diagram of a cell culture and expansion system for producing platelets in vitro FIGS. 2A and B depict cultures of hematopoietic stem cells.

The presently disclosed methods and systems are useful for the production of clinically useful quantities of megakaryocytes and platelets in vitro from different sources of progenitor or stem cells.

For the purposes of the present disclosure, the terms "stem cells" and "megakaryocyte progenitor cells" are interchangeable and refer to pluripotent, multipotent or unipotent stem cells or progenitor cells which are capable of differentiating into megakaryocytes and have the potential to produce platelets.

For the purposes of the present disclosure, the term "growth factors" refers to protein and non-protein factors which support the growth, maintenance, maturation, and differentiation of cells.

For the purposes of the present disclosure, the term "growth medium" refers to liquid or semi-solid aqueous medium which includes electrolytes, energy sources, growth factors and other materials necessary for the ex vivo culture of cells.

The process of platelet production from stem cells may be divided into several stages according to cell characteristics, internal cellular processes, and environmental signals. These stages include (1) stem cell replication; (2) megakaryocyte replication; (3) megakaryocyte maturation (increase in ploidy); (4) proplatelet formation; and (5) platelet release.

Each of these stages requires specific culture conditions and chemical factors to support the cell growth and differentiation. Factors involved in stage 1, hematopoietic stem cell (CD34$^+$ cell) expansion include, but are not limited to, aryl-hydrocarbon inhibitor/stem regenin-1, notch-ligand/delta-1, prostaglandin-E2, SALL4 gene induction or addition of exogenous SALL4 protein, recombinant human Hoxb4, stromal cell-derived factor-1 (SDF-1α), valproic acid, co-culture with endothelial cells, mesenchymal stem cells and/or OP-9 cells, tropoelastin, copper chelation, p38 inhibitors (such as SB203580), histone acetyltransferase inhibitors (HAI) (such as garcinol), Z-VAD-FMK, banana lectin, garlic lectin, interferon-a, thrombopoietin (TPO), stem cell factor (SCF), IL-3, IL-6, IL-11, and FLT-3 ligand (FLT-3l). Long-term culture for CD34+ and megakaryocyte progenitor expansion is conducted with a combination of growth factors. In one non-limiting embodiment, the growth factors are SCF (10-400 ng/ml, such as 100 ng/ml), TPO (10-250 ng/ml, such as 50 ng/ml), IGF-1 (10-100 ng/ml, such as 40 ng/ml), EPO (0.5-5 mg/ml, such as 2 mg/ml), dexamethasone (0.2-3 μM, such as 1 μM) and cholesterol-rich lipid mix (SIGMA® Chemical Co.). Cells are cultured for approximately 4-14 days and progenitors are selected by density or size exclusion methods and replated for expansion. This process can be repeated several times until higher progenitor expansion.

Factors involved in stage 2, megakaryocyte expansion include, but are not limited to, serotonin, arachadonic acid, Z-VAD-FMK, cell growth matrices such as MATRIGEL® (cell culture matrix, Discovery Labware Inc.), gelatin, fibrinogen, collagen, methylcellulose, and extracellular matrix gel, and cytokines such as TPO, SCF, IL-3, IL-6, and FLT-3l. Factors involved in stage 3, polyploidization/endomitosis include, but are not limited to: nicotinamide (vitamin B3), folic acid, vitamin B12, Rho/Rock inhibitors, Src inhibitors, stathmin inhibitor (staurosporine), Aurora-B inhibitors, Bcr-Abl inhibition, overexpression of cyclin D1, D3 and p19, phorbol 12-myristate 13-acetate (PMA), blebbistatin, MLCK inhibitors and increased oxygen concentration between about 15% and about 30% $PO_2$. In alternative embodiments, the $PO_2$ is between about 15% and about 25%, in another embodiment, the $PO_2$ is between about 17% and about 22%, and in another embodiment the $PO_2$ is about 20%. Factors involved in stage 4 and 5, proplatelet formation and platelet release include: fibrinogen, fibronectin, von Willebrand factor (vWF), Rho/Rock inhibitors, hirudin, heparin, Src inhibitors, Rac1 inhibitor, CDC42 inhibitor, Fas-ligand, PMA, nitric oxide, c-Myc inhibitors, and SDF-1α. Culturing cells in 3D matrices and applying shear stress with a flow system provides an improved environment for proplatelet formation and platelet release.

Hematopoietic stem cells are recruited into the megakaryocyte lineage by the cytokine thrombopoietin. TPO induces the stem cells to produce megakaryocyte- and platelet-specific proteins and to undergo the process of growth into the giant megakaryocyte cell. The megakaryocyte matures in a specific environment, or niche, of the bone marrow, which sustains megakaryocyte maturation. This allows the megakaryocyte to remain in one place and mature in an environment that strongly inhibits platelet formation. The developing megakaryocyte is also functionally restrained from producing platelets while in the bone marrow niche. The matrix protein collagen 1 mediates both of these effects. The baseline state of cultured megakaryocytes also appears to be characterized by inhibition of platelet formation. This is important in the marrow so that the platelets are not produced at the wrong time and place. When the megakaryocyte matures and migrates toward the blood vessels, this inhibition is lifted and it releases its platelets.

Megakaryocytes have the remarkable characteristic of doubling their nuclear and cellular contents without cell division through a process called endomitosis. Through endomitosis, the megakaryocyte grows to enormous size and may have more than 64 times the normal nuclear contents. The increase of nuclear contents, or polyploidy, plays a fundamental role in the platelet formation by allowing the cell to produce the large amounts of proteins and organelles necessary for platelet formation and function. Importantly, mature megakaryocytes also have vast quantities of extra cell membrane with which to make platelets. Inducing polyploidization can be achieved using the following reagents alone or in different combinations.

Rho/Rock Inhibitors.

The final steps of cell division require regulation of actin and myosin to form the cleavage furrow and contractile ring. The inhibition of actin and myosin during cytokinesis allows megakaryocytes to replicate DNA material without undergoing cell division. The Rho/Rock pathway signals through myosin light chain (MLC) and filamin and activates both stress fibers and lamellipodia formation. Y27632 inhibits the Rho/Rock pathway and consequently inhibits myosin activation and the contractile ring formation, presumably allowing the megakaryocyte to undergo polyploidization. Exemplary Rho/Rock inhibitors include, but are not limited to, Y27632, thiazovivin, GSK429286A, fasudil HCl, Y39983, Wf-536, SLx-2119, Azabenzimidazole-aminofurazans, DE-104, and H-1152P.

Nicotinamide (NIC).

Decreases in p53 activity are responsible for accelerated DNA synthesis, higher ploidy and delayed apoptosis. NIC increases p53 activity and thus increases endomitosis and megakaryocyte polyploidization.

Src-Inhibitors.

The inhibition of Src family kinases increases megakaryocyte polyploidization through the Lyn/Fyn pathway and inhibition of actin polymerization. Exemplary Src inhibitors include, but are not limited to, saracatinib (AZD0530), bosutinib (SKI-606), danusertib (PHA-739358), NVP-BHG712, quercetin (sophoretin), PCI-32765, KX2-391, AP23846, and PP2.

Aurora-B Inhibitor.

Aurora-B is responsible for controlling the microtubules formation and consequent chromosome separation during mitosis. Its inhibition increases microtubule destruction through stathmin and mitotic centromere-associated kinesin (MCAK) action. Exemplary Aurora-B kinase inhibitors include, but are not limited to, AMG 900, AT9283, Aurora A Inhibitor I, AZD1152, AZD1152-HQPA (barasertib), CCT129202, CYC116, danusertib (PHA-739358), ENMD-2076, GSK1070916, hesperadin, JNJ-7706621, KW-2449, MLN8054, MLN8237 (alisertib), PF-03814735, PHA-680632, SNS-314, TAK-901, VX-680 (MK-0457, tozasertib), and ZM-447439.

Myosin Light Chain Kinase Inhibitor.

Myosin light chain kinase (MLCK) is involved in late stages of myosin stimulation; it acts through MLC and is responsible for stress fibers activation and lamellipodia formation. Exemplary MLCK inhibitors include, but are not limited to, A3 HCl, Gö 7874 HCl, InSolution™ K-252a (*Nocardiopsis* sp.), K-252a (*Nocardiopsis* sp.), K-252b (*Nocardiopsis* sp.), ML-7 HCl, ML-9 HCl, MLCK inhibitor peptide 18, piceatannol, and staurosporine (*Streptomyces* sp.).

Phorbol 12-Myristate 13-Acetate (PMA).

Protein kinase C (PKC) is involved in megakaryocyte differentiation and growth and its activation through PMA increases cell ploidy.

Blebbistatin.

Blebbistatin inhibits myosin II and consequently the last steps of cytokinesis and cell division, thus allowing the cell to undergo polyploidization and increase the nuclear material.

Stathmin Inhibitor (Staurosporine).

Stathmin is involved in microtubule formation and the final steps of cytokinesis. Its inhibition blocks cell division and increases megakaryocyte ploidy.

Increased oxygen concentration during culture increases megakaryocyte polyploidization.

As the megakaryocyte matures, its surface receptors change, making it less adhesive to the bone marrow niche, but ready for residence near the blood vessels in the perivascular niche. Once the megakaryocyte is mature it is lured out of the bone marrow niche toward the perivascular niche by signals from the vascular niche, such as SDF-1α. Importantly, as it leaves the bone marrow niche the megakaryocyte is freed from the inhibition of platelet formation. Near the blood vessels, the megakaryocyte also encounters extracellular proteins that signal the cell to make platelets. Platelet formation is initiated by the extrusion of very long cytoplasmic processes called proplatelets, which contain all of the platelet elements. These processes extend through the blood vessel walls into the blood stream and are released by the shear forces of the flowing blood.

Rho/Rock pathway inhibitors increase proplatelet formation in cultured megakaryocytes. The mechanism involves reversal of the bone marrow niche-induced inhibition of proplatelet formation. Inducing megakaryocyte apoptosis with nitric oxide (such as, but not limited to, S-nitrosoglutathione) and/or caspase activators (such as, but not limited to, Fas-ligand) also increases megakaryocyte proplatelet formation and platelet release. PKC activation with PMA induces megakaryocyte differentiation and consequently increases proplatelet formation. Rac1 activation, CDC42 activation, hirudin and c-Myc inhibition also increase proplatelet formation.

A constant flow of nutrient-rich medium is important in the process of increasing proplatelet formation and platelet release and is applied with a pump to the megakaryocyte culture in a shear stress range between about 100 µl/min and about 500 µl/min. In other embodiments, the shear stress is in a range of about 200 µl/min to about 400 µl/min, about 150 µl/min to about 350 µl/min, about 250 µl/min to about 350 µl/min, about 250 µl/min to about 450 µl/min, or about 100 µl/min to about 400 µl/min. Platelets are collected after release in a specific platelet bag with preservative solutions. Produced megakaryocytes and platelets are analyzed for antigen expression (CD41, CD42b, CD61), activation (P-selectin), cultured for contamination, CFU-MEG grown assay and flow analysis of ploidy.

Disclosed herein are methods and systems for producing platelets in artificial systems in which megakaryocyte progenitor cells are grown and matured in experimental matrices containing proteins found in the bone marrow niche environment. The creation of defined physical and chemical environments drives megakaryocyte maturation and subsequent platelet formation. The defined environments are designed into self-contained modules that are used sequentially in a bioreactor to efficiently generate platelets from stem cells.

The term "megakaryocyte progenitor cells," as used herein, refers to hematopoietic stem cells committed to at least the megakaryocyte lineage and includes, but is not limited to, cells in the umbilical cord blood, bone marrow, and peripheral blood as well as hematopoietic stem cells, human embryonic stem cells, and induced pluripotent stem cells.

In one embodiment, a platelet production device is used to increase the cell expansion of stem cells and/or megakaryocyte progenitors. A flow diagram of an exemplary platelet production device for producing platelets in vitro can be found in FIG. 1. The bioreactors, vessels, chambers, reservoirs, niches, and bags of the platelet production device are connected by a series of sterile tubing which may optionally contain pumps, valves, membranes, filters, and sensors as appropriate.

The platelet production device 100 comprises a bioreactor 102 into which a source of stem cells is placed. The stem cells are megakaryocyte-producing progenitor cells including, but are not limited to, hematopoietic stem cells (from umbilical cord blood, bone marrow, and/or peripheral blood), embryonic stem cell lines, induced pluripotent stem cells, and fibroblasts. The progenitor cells are optionally enriched for CD34+ cells prior to placement in the bioreactor 102. The bioreactor 102 further contains a suitable first growth media including appropriate growth factors.

After a culture period of between about 1 week and about 1 month, the expanded progenitor cells are transferred from bioreactor 102 into a maturation chamber 110 for maturation into large, polyploidy megakaryocytes. In alternative embodiments, the culture period is between about 2 weeks and about 1 month, about 3 weeks and about 1 month, between about 2 weeks and about 3 weeks, or between about 1 week and about 3 weeks. Maturation chamber 110 comprises an artificial bone marrow niche environment which comprises a cell growth matrix such as, but not limited to, MATRIGEL®, gelatin, fibrinogen, collagen, methylcellulose, and extracellular matrix gel. MATRIGEL® is a gelatinous protein mixture secreted by Engelbreth-Holm-Swarm (EHS) mouse sarcoma cells and mimics the complex extracellular environment found in many tissues. This environment also contains all the factors necessary for maturation and polyploidization of the megakaryocytes including a plurality of factors selected from the group consisting of nicotinamide (vitamin B3), folic acid, vitamin B12, Rho/Rock inhibitors, Src inhibitors, stathmin inhibitors, Aurora-B inhibitors, Bcr-Abl inhibition, induction of cyclin D1, D3 and p19, phorbol 12-myristate 13-acetate (PMA), blebbistatin, Rac1 inhibitors, CDC42 inhibitors, and MLCK inhibitors. The culture environment in maturation chamber 110 is also adapted to have an increased oxygen concentration compared to standard cell culture conditions. The increased oxygen concentration is between 10% and 30% $PO_2$. In alternative embodiments, the $PO_2$ is between about 15% and about 25%, in another embodiment, the $PO_2$ is between about 17% and about 22%, and in another embodiment the $PO_2$ is about 20%. The expanded megakaryocyte progenitor cells are maintained in maturation chamber 110 for a period of time, such as period of time between about 2 days and 12 days of culture, until a population of mature and polyploid megakaryocytes is obtained. In alternative embodiments, the culture period is between about 3 days and about 11 days, between about 4 days and about 10 days, between about 5 days and about 11 days, between about 6 days and about 11 days, between about 7 days and about 11 days, between about 8 days and about 11 days, between about 5 days and about 9 days, and between about 6 days and about 8 days.

Mature and polyploid megakaryocytes are then transferred to cell separation chamber 120 which contains a concentration gradient of bovine serum albumin (BSA) 124. The concentration gradient of BSA separates the megakaryocytes according to their size. Thus, large, mature polyploid megakaryocytes 126 are concentrated in the bottom of the chamber and the small, immature megakaryocytes 122 are at the surface. The mature megakaryocytes are then transferred to the platelet production module 135 and the immature megakaryocytes are passaged through recirculating loop 140 back to the maturation chamber 110 for further maturation.

The mature megakaryocytes are passed into platelet production chamber 135 which is comprised of a series of platelet release chambers 130, each platelet release chamber 130 containing a 3D matrix or scaffold 150 with pores between about 2 μm and about 6 μm and coated with factors that stimulate proplatelet formation and platelet release. In alternative embodiments, the 3D matrix comprises pores between about 3 μm and about 5 μm, and between about 3.5 μm and about 4.5 μm. Exemplary matrices include, but are not limited to, gelatin, MATRIGEL®, ALGIMATRIX® (cell culture matrix, Invitrogen Corp.), alginate, polystyrene, and polyester in the form of beads, mesh, felt or other 3D structures coated with a plurality of growth factors including, but not limited to, fibrinogen, fibronectin, von Willebrand factor (vWF), Fas-ligand, PMA, nitric oxide, Rho/Rock inhibitors, Src inhibitors, Rac1 inhibitors, CDC42 inhibitors, SDF-1α, hirudin, heparin, c-Myc inhibitors, MLCK inhibitors, and Rho/Rock inhibitors. Platelet production chamber 135 also includes a reservoir 138 containing a third growth media. Each of the platelet release chambers 130 are attached to a syringe pump 160 that provides a flow and shear stress to the proplatelet formation environment. The platelet release chambers are additionally connected to syringe pump 170 and reservoir 175 which provides tangential flow (shear stress) for releasing and collecting platelets. Released platelets are collected and stored in platelet collection chamber 180.

In one embodiment, the bioreactors, vessels, chambers and bags are cell collection bags, such as sterile blood collection bags known to persons of ordinary skill in the blood banking arts. In other embodiments, the vessels, chambers and bags are sterile biocompatible containers of any design.

Also disclosed herein is a method for the production of platelets in an artificial in vitro system. In one embodiment, the system is a platelet production device described herein. However, other platelet production devices or cell culture systems are within the scope of the claims and the system is not limited to the platelet production device depicted herein.

The method comprises (1) culturing the stem cells under conditions to expand the population of megakaryocyte progenitor cells; (2) differentiating and maturing the megakaryocyte progenitor cells into mature megakaryocytes; (3) isolating the mature megakaryocytes, (4) producing platelets from the mature megakaryocytes, and (5) collecting the platelets.

For the culture and expansion step, the megakaryocyte progenitor cells are cultured under conditions which include a first growth media, and appropriate oxygen and pH levels, In particular, a higher $pO_2$ concentration and pH than standard cell culture conditions are necessary for appropriate megakaryocyte yield. Suitable $PO_2$ concentrations are in the range of about 10% and about 30% $PO_2$, and suitable pH is in the range of about 7.2 and about 7.6. In alternative embodiments, the $PO_2$ is between about 15% and about 25%, in another embodiment, the $PO_2$ is between about 17% and about 22%, and in another embodiment the $PO_2$ is about 20%. In alternative embodiments, the pH is between about 7.3 and about 7.5, between about 7.2 and about 7.4. In another embodiment, the pH is about 7.4. The first growth media includes a plurality of growth factors selected from the group consisting of aryl-hydrocarbon inhibitor/stem regenin-1, notch-ligand delta-1, prostaglandin-E2, SALL4 gene activators, histone acetyltransferase inhibitor, Hoxb4 activators, SDF-1α, valproic acid, p38 inhibitors, co-culture with mesenchymal stem cells and/or OP-9 cells, tropoelastin, copper chelation, Z-VAD-FMK, banana lectin, garlic lectin, interferon-α, TPO, SCF, IL-3, IL-6, IL-11, and FLT-3l. In one embodiment, the culture and expansion step is performed in a culture vessel, for example the bioreactor 102 of FIG. 1.

Optionally the megakaryocyte progenitor cells are enriched for CD34+ cells prior to expansion. Methods for enrichment of CD34+ cells are known to persons of ordinary skill in the art. One exemplary method of enrichment of CD34+ cells is using a negative selection method. An exemplary negative selection method is a rapid cell separation method to isolate highly purified cells directly from mixed cell populations including blood. An exemplary method uses ROSETTESEP® technology (STEMCELL® Technologies) which comprises tetrameric antibody complexes which aggregate unwanted cells with red blood cells present in the sample, forming immunorosettes, which are removed by density centrifugation. The desired cells are not labeled with antibody and are immediately ready for culture.

In one embodiment, the stem cell expansion and culture step is conducted for about 15 to about 30 days. In alternative embodiments, the stem cell expansion and culture step is conducted for about 15 to about 25 days, about 20 to about 30 days, about 17 to about 28 days, about 19 to about 26 days, about 21 to about 24 days, and about 22 to about 28 days.

The expanded megakaryocyte progenitor cells are then cultured under conditions to differentiate and mature the progenitors into mature megakaryocytes. These conditions mimic the bone marrow niche environment in which megakaryocytes mature in vivo and the artificial bone marrow niche environment includes both a cell growth matrix and a second growth medium containing a plurality of growth factors. Exemplary cell growth matrices include, but are not limited to, MATRIGEL®, gelatin, fibrinogen, collagen, methylcellulose, and extracellular matrix gel. The plurality of growth factors is selected from the group consisting of serotonin, arachidonic acid, Z-VAD-FMK, TPO, SCF, IL-3, IL-6, FLT-3l, nicotinamide (vitamin B3), folic acid, vitamin B12, Rho/Rock inhibitors, Src inhibitors, Aurora-B inhibitors, Bcr-Abl inhibitors, induction of cyclins D1, D3 and p19, PMA, blebbistatin, and MLCK (Myosin light chain kinase inhibitor peptide 18) inhibitors. In one embodiment, the differentiating and maturing step is performed in the maturation chamber 110 of FIG. 1.

In another embodiment, the artificial bone marrow niche environment further includes mesenchymal stem cells. An exemplary source of mesenchymal stem cells is bone marrow. The mesenchymal stem cells can be mixed with the megakaryocyte progenitor cells or segregated from the megakaryocyte progenitor cells by a porous membrane which allows the passage of cellular materials (but not whole cells) from the mesenchymal stem cells to the megakaryocyte progenitor cells.

In one embodiment, the differentiation and maturation step is conducted for about 8 to about 11 days. In alternative embodiments, the differentiation and maturation step is conducted for about 9 to about 10 days, from about 8 to 10 days, or about 9 to 11 days.

The mature megakaryocytes are isolated on a density gradient before entering the platelet production phase. Mature megakaryocytes enter the platelet production phase and immature megakaryocytes are returned to the artificial bone marrow niche for further maturation.

The mature megakaryocytes are then cultured under conditions which induce the production of platelets. The megakaryocytes are transferred to chambers in which a filter or membrane is present on one surface to allow the free flow of a third growth media from a reservoir, retaining megakaryocytes, and allowing platelets to pass through. The third growth media contains a plurality of growth factors selected from the group consisting of, fibrinogen, fibronectin, vWF, Fas-ligand, PMA, nitric oxide, Rho/Rock inhibitors, Src inhibitors, MLCK inhibitors, hirudin, heparin, c-Myc inhibitors and SDF-1α. In one embodiment, the platelet production step is conducted in platelet production chamber 135 of FIG. 1.

In one embodiment, the proplatelet formation and platelet collection step is conducted for about 1 to about 2 days.

The platelets produced are then collected in a suitable vessel for further use. In one embodiment, the vessel is platelet bag 180 of FIG. 1.

The platelets produced by the system and method disclosed herein are suitable for use in a variety of diseases and conditions including, thrombocytopenia, treatment of infection, support during surgery, treatment of platelet defects, bleeding conditions, and others.

EXAMPLES

Example 1

Isolation and Culture of Stem Cells

Platelets can be derived from different sources of stem cells. Described herein are methods for selecting and growing stem cells from different sources.

Human Embryonic Stem Cells.

HeSC are derived from cell lines including, but not limited to, H1, H7, H9, HuES-3, MA01, MA40 and MA09. The HeSC are differentiated into hemangioblasts/blasts cells with the addition to serum-free medium of bone morphogenic protein 4 (BMP-4), vascular endothelial growth factor (165aa, VEGF165), stem cell factor (SCF), thrombopoietin (TPO) and FLT-3 ligand (FLT-3l). The cultured hemangioblasts can be co-cultured with mesenchymal stem cells (MSC) and are finally differentiated into megakaryocytes with cytokines such as TPO, SCF, IL-6, IL-9, IL-11, VEGF, and fibroblast growth factor (FGF).

Induced Pluripotent Stem Cells.

IPSC are derived from somatic and mature cells and transfected with genes that code transcriptional factors known to maintain pluripotency including, but not limited to, Oct3/4, Sox2, Nanog, Lin28, c-Myc, and Klf-4. The transformation of mature cells into hematopoietic progenitor is also possible using just one gene modification (Oct4). Gene transfection is performed using virus (adenovirus, lentivirus) and/or plasmids. The immature and pluripotent cells are then co-cultured with MSC and cytokines such as TPO, SCF, IL-3, and IL-9 in medium to differentiate the IPSC into hematopoietic progenitors and megakaryocytes.

Hematopoietic Stem Cells.

Hematopoietic stem cells are collected from the bone marrow, from peripheral blood with an apheresis machine or from umbilical cord blood (UCB).

UCB is collected from the umbilical cord vein right after delivery. Approximately 100 ml are collected, stored with anticoagulant (CPD-A) and used within 24 hours. Total leukocytes are separated from red blood cells by sedimentation with dextran. The lymphocytes are separated from the total leukocytes by density separation with FICOLL® (cell separation copolymer, GE Healthcare companies). Stem cells, which are identified by the $CD34^+$ surface protein, are isolated using anti-$CD34^+$ antibodies linked to metal beads, which bind to the stem cells and are retrieved with a magnet. Hematopoietic stem cells can also be selected with a second negative selection method. The negative selection method involves using ROSETTESEP® (STEMCELL® Technologies) during the preparation and has a lower final $CD34^+$ purity (around 10%). Thus, this method allows the cells to grow surrounded by other hematopoietic cells, in an environment closer to the bone marrow niche.

The CD34+ cells are then cultured in the presence of one or more factors selected from the group consisting of TPO, SCF, IL-11, IL-6, and IL-3 for expanding and differentiating the stem cells toward megakaryocytopoiesis.

Fibroblasts.

Fibroblasts can be directly differentiated into hematopoietic stem cells by activating specific gene of immaturity. Mature fibroblasts can be transduced with genes, for example Oct-4, allowing them to express characteristics of hematopoietic progenitors and, therefore, be differentiated into megakaryocytes and platelets.

Hematopoietic stem cells are laboratory expanded to increase the number of progenitors and consequently increase the platelet production. Four different matrices are evaluated for support of megakaryocytopoiesis including 1) gelatin; 2) MATRIGEL®, a mixture of extracellular matrix proteins derived from cellular basement membranes; 3) methylcellulose, a gelatin-like liquid used in stem cell culture; and 4) polyester mesh scaffolding, which is a surgical grade membrane that has been used for stem cell culture. Different concentrations of methylcellulose, MATRIGEL® or gelatin are used. These are mixed with the cytokines described above, as well as different concentrations of collagen I. The polyester mesh can be incubated with different concentrations of soluble collagen I. In alternative embodiments, cells are culture expanded prior to culture in the matrix.

In another embodiment, the megakaryocytes are cultured in association with mesenchymal stem cells, also derived from UCB. These mesenchymal stem cells can differentiate into bone and cartilage. They have recently been described as a means of mimicking the microenvironment of the bone marrow niche. In another embodiment, the megakaryocyte growth is maximized on the bone marrow cells, and then the megakaryocytes are transitioned to growth on only the secreted matrix of the bone marrow cells. The bone marrow cells are grown on culture dishes and then the cells are removed, leaving behind the secreted proteins. Cord blood-derived CD34+ stem cells or megakaryocytes are then placed directly onto a plate that is coated with a layer of bone marrow stroma cells in the presence of cytokines. The growing megakaryocytes are evaluated daily to characterize their size, shape, nucleus and differentiation capacity.

Example 2

Effect of CD34+ Negative Selection on Megakaryocyte Expansion

Umbilical cord blood was obtained and the CD34+ cells were selected by negative selection (ROSETTESEP®) or positive selection. The positive selection method is based on the separation of stem cells using beads and magnetic columns. Beads attach to specific stem cell surface markers and are positively selected with the magnetic columns.

Figure 2A:
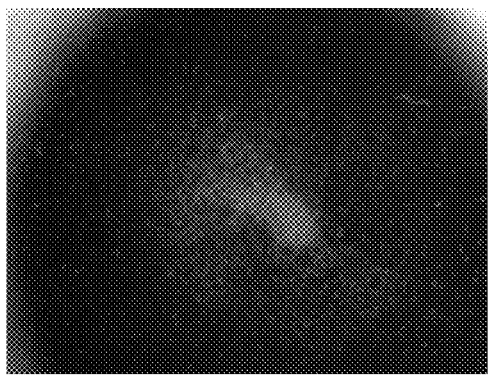
Figure 2B:
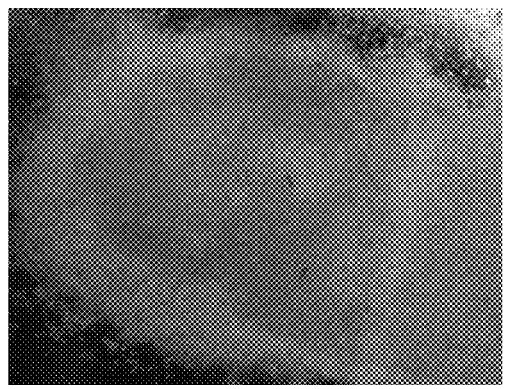
Figure 3A:
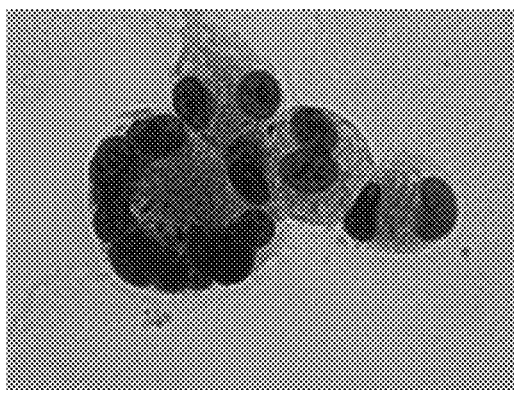
FIGS. 3A and B depict megakaryocytes differentiated from the culture in FIG. 2.
Figure 3B:
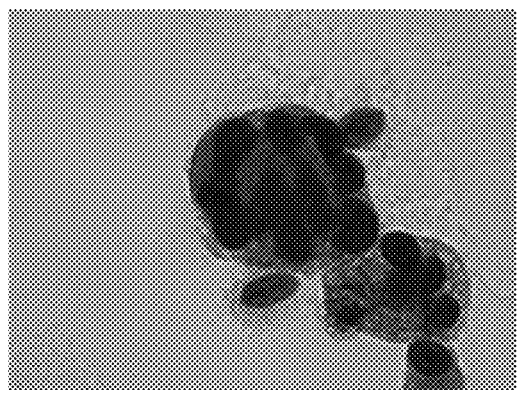
Figure 4A:
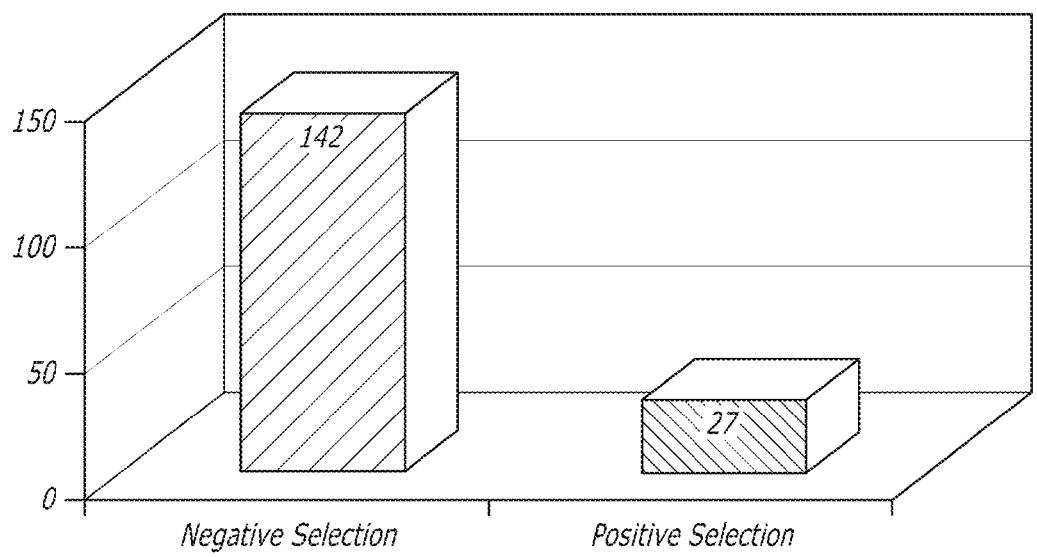
FIGS. 4A and B depicts the fold expansion (FIG. 4A) and surface antigen expression (FIG. 4B) of megakaryocytes expanded from negatively selected CD34+ umbilical cord blood. The positive selection bar in FIG. 4A is a historical control.
Figure 4B:
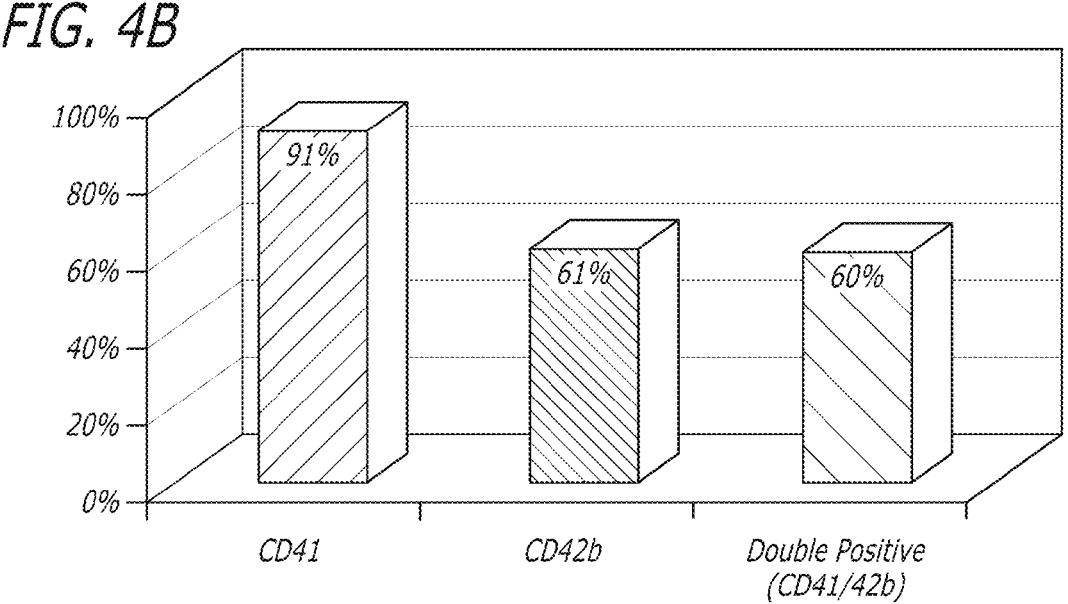

After negative selection, $1 \times 10^5$ total nucleated cells (TNC) and $7 \times 10^3$. CD34$^+$ cells were plated in 24 well plates at a concentration of $2 \times 10^5$ cells/ml (FIG. 2). STEMSPAN® medium (tissue culture medium, STEMCELL® Technologies) was used for culture with added thrombopoietin (50 ng/ml) and stem cell factor (50 ng/ml) as cytokines. Fresh medium was added to the culture every 3 days and the cells were replated on day 5 of culture. The culture was carried out at 37° C. with 5% $CO_2$ and ambient oxygen. The cultured cells are depicted in FIGS. 3 and 4. The cells were analyzed by flow cytometry on day 11 of culture for CD41 and CD42b antigen expression as well as their ploidy. A BD Canto flow machine was used for analysis. The positive selection results for comparison were selected from the literature.

The culture was started with $7 \times 10^3$ CD34+ cells and the final yield of megakaryocytes was $1 \times 10^6$ cells with a fold expansion of 142. The antigen expression analysis of the megakaryocytes demonstrated that CD41 and CD42b were expressed on 91% and 61% of the cells, respectively, and 60% of the cells were double positive (CD41/CD42b). The ploidy analysis showed that 65% of the megakaryocytes were 2N, 20% were 4N and 15% were above 4N.

According to the literature, the CD34+ expression in the positive selected cell population should be over 90% and the fold expansion with different protocols for megakaryocytes was from 4 to 27 fold.

The negative selection technique allows the CD34+ stem cells to grow under the influence of other hematopoietic cells and provides a better expansion microenvironment. The high megakaryocyte fold-expansion (142-fold) and CD41 expression (91%) achieved in this experiment shows the importance of the microenvironment and the cell-to-cell signaling during megakaryocyte expansion.

Example 3

Driving Proplatelet Formation with the Cytokine SDF-1α

The cytokine SDF-1α mobilizes the mature megakaryocyte out of the bone marrow niche and is used to transition the mature megakaryocytes into an optimal culture environment. Initially, the cells are physically transferred from the maturation culture to a new culture dish containing SDF-1α within a 3D matrix. The SDF-1α lures the mature megakaryocytes into the 3D matrix. Exemplary 3D matrices include, but are not limited to, gelatin, MATRIGEL®, ALGIMATRIX®, polystyrene and polyester mesh. The effects on megakaryocyte survival and proplatelet formation are measured. The proplatelet formation matrix is then subjected to conditions suitable for proplatelet formation.

Example 4

Driving Proplatelet Formation with Extracellular Signals

Figure 5A:
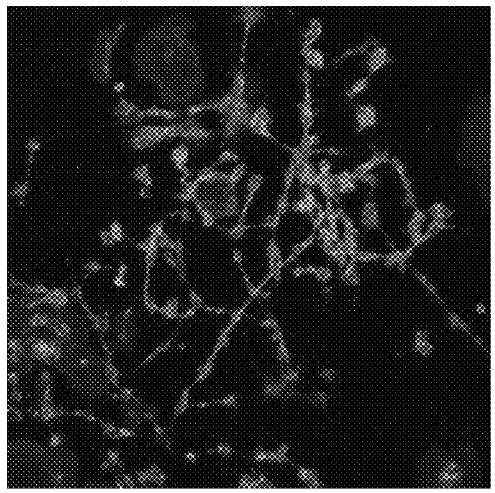
FIGS. 5A-C depict proplatelet formation and platelet release from mature megakaryocytes.
Figure 5B:
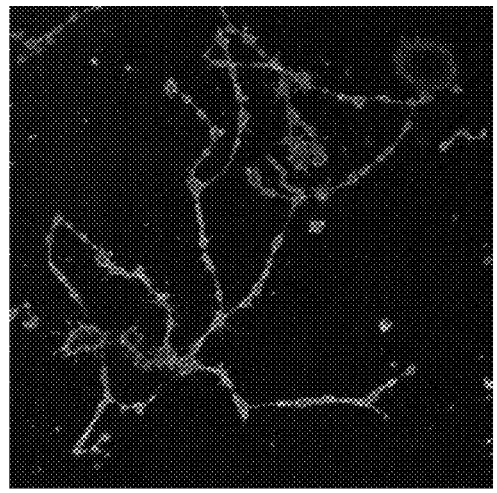
Figure 5C:
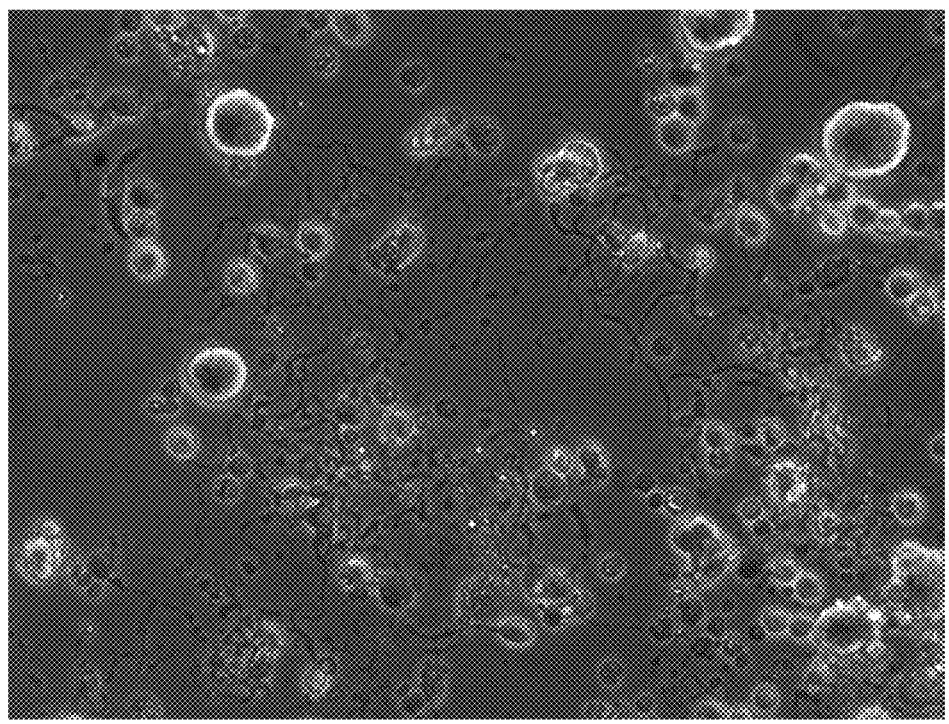
Figure 6:
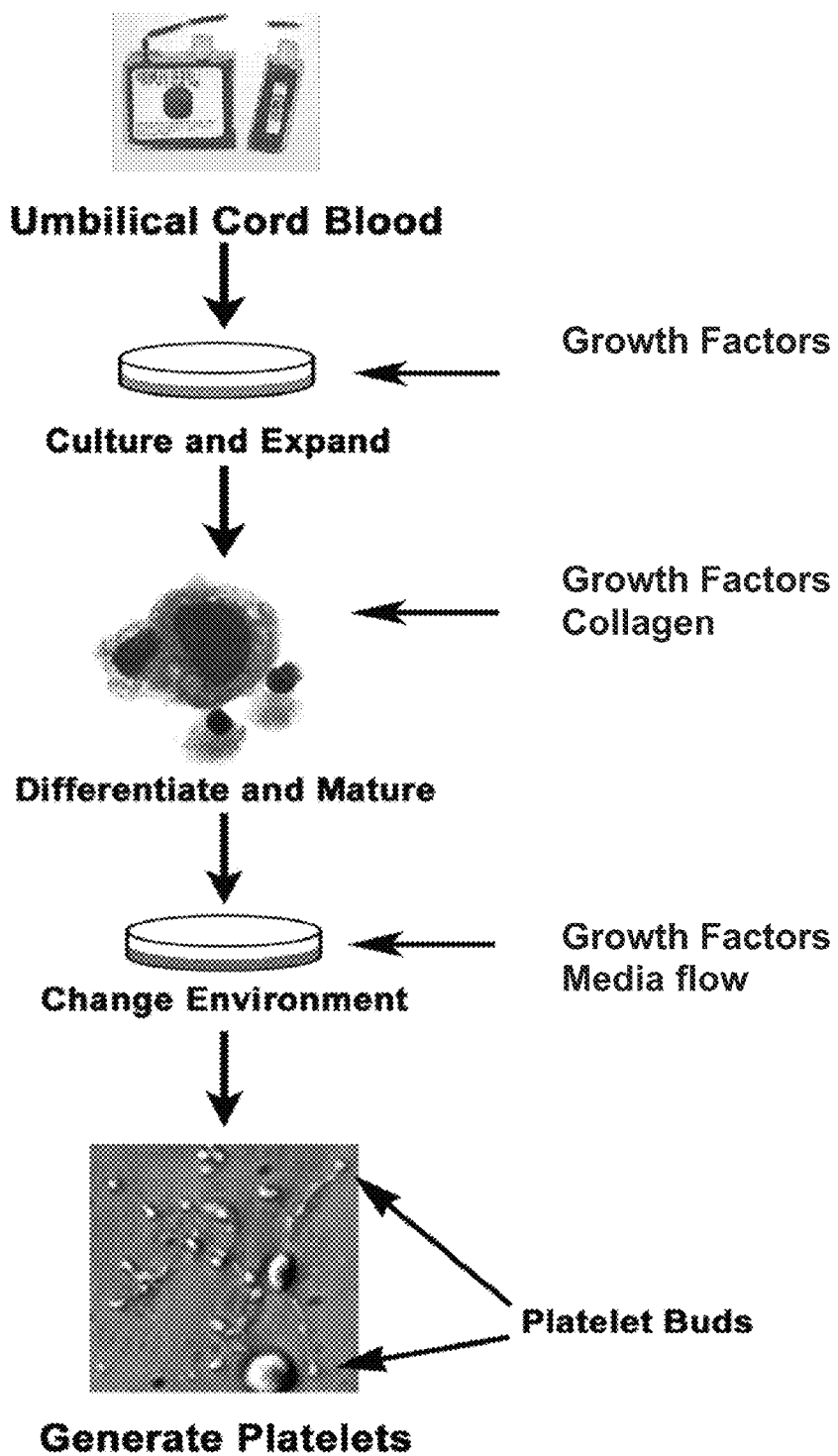
FIG. 6 depicts a flow diagram of one embodiment of the disclosed method for producing platelets in vitro.

Extracellular matrix proteins and other factors are introduced into the proplatelet formation culture environment to simulate the vascular niche. These proteins include, but are not limited to, fibrinogen, fibronectin, vWF, Fas-ligand, PMA, nitric oxide, Rho/Rock inhibitors, Src inhibitors, Rac1 activator, Cdc42 activator, MLCK inhibitors, hirudin, heparin and c-Myc inhibitors Each of these factors increases both the proportion of megakaryocytes producing proplatelets and the number of processes per megakaryocyte. Membranes with pores between 3 µm and 5 µm are coated with these reagents and the megakaryocytes are stimulated to release proplatelets and platelets through the pores. FIG. 5A-C depicts extended proplatelets budding from the mature megakaryocytes and platelets being released after contact with fibrinogen.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for producing platelets for clinical transfusion in vitro comprising:
   (1) culturing stem cells in a first growth medium to produce a megakaryocyte progenitor cell population, wherein the first growth medium comprises aryl-hydrocarbon inhibitor/stem regenin-1 and notch-ligand delta-1;
   (2) maturing the expanded megakaryocyte progenitor cells in an artificial bone marrow niche environment comprising a second growth medium in the presence of an oxygen concentration between about 10% and about 30% $PO_2$ to differentiate the megakaryocyte progenitor cells into megakaryocytes, wherein the second growth medium comprises thrombopoietin (TPO), stem cell factor (SCF), nicotinamide, and a Rho/Rock inhibitor;
   (3) isolating the mature megakaryocytes;
   (4) culturing the mature megakaryocytes in a three-dimensional matrix and a third growth medium and in the presence of an oxygen concentration between about 10% and about 30% $PO_2$ and a shear stress between about 100 and 400 μl/min to produce platelets, wherein the third growth medium comprises fibrinogen, fibronectin, von Willebrand factor (vWF), an MLCK inhibitor, a Rho/Rock inhibitor, and nicotinamide; and
   (5) collecting the platelets in a number suitable for transfusion.

2. The method of claim 1, wherein the stem cells are selected from the group consisting of hematopoietic stem cells, induced pluripotent stem cells, embryonic stem cells, and fibroblasts.

3. The method of claim 2, wherein the hematopoietic stem cells are obtained from the bone marrow, peripheral blood, or cord blood.

4. The method of claim 1, wherein the stem cells are enriched for CD34$^+$ cells prior to culture-expansion.

5. The method of claim 1, wherein the first growth medium further comprises additional growth factors selected from the group consisting of prostaglandin-E2, SALL4 gene activators, Hoxb4 activators, stromal cell-derived factor-1 (SDF-1α), histone acetyl transferase inhibitors, valproic acid, tropoelastin, copper chelation, Z-VAD-FMK, banana lectin, garlic lectin, interferon-α, TPO, p38 inhibitors, SCF, dexamethasone, lipids, IGF-1, erythropoietin (EPO), IL-3, IL-6, IL-11, and FLT-3 ligand (FLT-3l).

6. The method of claim 5, wherein the growth factors are IL-3, IL-6, and IL-11.

7. The method of claim 1, wherein the second growth medium further comprises additional growth factors selected from the group consisting of serotonin, arachidonic acid, Z-VAD-FMK, IL-3, IL-6, and FLT-3l.

8. The method of claim 1, wherein the cell growth matrix is selected from the group consisting of extracellular matrix extracts, extracellular matrix gels, gelatin, fibrinogen, collagen, methylcellulose, and combinations thereof.

9. The method of claim 1, wherein the artificial bone marrow niche further contains mesenchymal stem cells and/or endothelial cells.

10. The method of claim 1, wherein the third growth medium comprises a plurality of growth factors selected from the group consisting of Fas-ligand, PMA, nitric oxide, Src inhibitors, SDF-1α, folic acid, vitamin B12, Aurora-B inhibitors, Bcr-Abl inhibitors, phorbol 12-myristate 13-acetate (PMA), and blebbistatin.

11. The method of claim 1, wherein the first growth medium further comprises mesenchymal stem cells and/or OP-9 cells.

\* \* \* \* \*